United States Patent [19]
Kroll

[11] Patent Number: 5,334,219
[45] Date of Patent: Aug. 2, 1994

[54] IMPROVED METHOD AND APPARATUS FOR SEPARATE-CAPACITOR CARDIOVERSION

[75] Inventor: Mark W. Kroll, Minnetonka, Minn.

[73] Assignee: Angeion Corporation, Plymouth, Minn.

[21] Appl. No.: 866,368

[22] Filed: Apr. 9, 1992

[51] Int. Cl.$^5$ .............................................. A61N 1/38
[52] U.S. Cl. ...................................................... 607/5
[58] Field of Search ...................................... 607/5, 7

[56] References Cited

U.S. PATENT DOCUMENTS

| | | | |
|---|---|---|---|
| 4,693,253 | 9/1987 | Adams | 607/4 |
| 4,823,796 | 4/1989 | Benson | 607/7 |
| 4,830,006 | 5/1989 | Haluska | 607/5 |
| 5,014,697 | 5/1991 | Pless et al. | 607/7 |
| 5,188,105 | 2/1993 | Keimel | 607/5 |

FOREIGN PATENT DOCUMENTS 0272021  7/1964  Austria ..................... 607/5

OTHER PUBLICATIONS

A. C. Guyton and J. Satterfield, "Factors concerned in defibrillation of the heart, particularly through the unopened chest," *Am J. of Physiology*, vol. 167, p. 81, 1951.

J. C. Schuder, G. A. Rahmoeller, and H. Stoecke, "Transthoracic ventricular defibrillation with triangular and trapezoidal waveforms," *Circ Res*, vol. 19, p. 689–694, Otct. 1966.

W. A. Tacker, L. A. Geddes, J. McFarlane, et al, "Optimum current duration for capacitor–discharge defibrillation of canine ventricles," *J. Applied Physiology*, vol. 27, #4, pp. 480–483, Oct. 1969.

J. C. Schuder, H. Stoeckle, J. A. Wes, et al. "Transthoracic ventricular defibrillation in the dog with truncated and untruncated exponential stimuli," *IEEE Trans. Biom. Eng.*, vol. BME-18 #6, pp. 410-415, Nov. 1971.

G. Weiss, "Sur la possibilite de rendre comparable entre eux les appareils survant a l'excitation electrique," *Arch. Ital. de Biol.*, vol. 35, pp. 413-446, 1901.

J. D. Bourland, W. A. Tacker, and L. A. Geddes, "Strength duration curves for trapezoidal waveforms of tilts for transchest difibrillation in animals," *Med. Instr.*, vol. 12 #1, pp. 38–41, 1978.

J. D. Bourland, W. A. Tacker, L. A. Geddes et al, "Comparative efficacy of damped sine wave and square wave current for transchest ventricular difibrillation in animals," *Medical Instrum.*, vol. 12, #1, pp. 38–41, 1978.

J. A. Pearce, J. D. Bourland, W. Neilsen, et al, "Myocardial stimulation with ultrashort duration curent pulses," *PACE*, vol. 5, pp. 52–58, Jan.–Feb. 1982. a P. D. Chen, P. D. Wolf, and F. J. Claydon, "The potential gradient field created by epicardial defibrillation electrodes in dogs," *Circulation*, vol. 74, pp. 626–635, Sep. 1986.

H. Fredericq, "Chronaxie: Testing excitability by means of a time factor," *Physiol. Rev.*, vol. 8, pp. 501–545, 1928.

*Primary Examiner*—William E. Kamm
*Attorney, Agent, or Firm*—Patterson & Keough

[57] ABSTRACT

A implantable cardioverter-defibrillator employs, as a battery-saving design, a capacitance about nine time smaller than a typical defibrillation capacitor to provide an optimal-duration pulse of about 1 millisecond with a waveform based on the system time constants, i.e. the tissue resistance, the value of the capacitor and the heart's cardioversion chronaxie, a characteristic time associated with the stimulation of myocardial tissue. For higher-energy defibrillation, a second small capacitance is added to boost the energy.

30 Claims, 2 Drawing Sheets

IMPROVED METHOD AND APPARATUS FOR SEPARATE-CAPACITOR CARDIOVERSION

CROSS REFERENCES TO CO-PENDING APPLICATIONS

This patent application relates to U.S. patent application Ser. No. 07/808,722, filed Dec. 17, 1991, entitled "Small Capacitance Defibrillation Process"; U.S. patent application Ser. No. 07/835,836, filed Feb. 18, 1992, entitled "Optimal Pulse Defibrillator"; U.S. patent application Ser. No. 07/866,460, filed Apr. 9, 1992, entitled "Narrow Pulse Cardioversion Method for Implantable Cardioverter Defibrillator"; and, U.S. patent application Ser. No. 07/863,738, filed Apr. 6, 1992, entitled "Method and Apparatus for Far-Field Tachycardia Termination" the disclosure of each of which is incorporated by reference in this application.

BACKGROUND OF THE INVENTION

1. Field of the Invention

The present invention relates generally to cardioversion tachycardia-termination processes, and more particularly, to more nearly optimal cardioversion pulses delivered from a separate capacitor smaller than the defibrillation capacitor where this feature is incorporated in an implantable cardioverter-defibrillator (ICD).

2. Description of the Prior Art

Implantable cardioverter-defibrillator systems now on the market and in use for clinical studies employ capacitors of 120 to 180 microfarads to deliver a defibrillation pulse that usually has an energy of about 20 joules. They use the same capacitor to deliver a cardioversion pulse, and typically, use the same pulse duration for cardioversion as for defibrillation, with the former having an energy in the range of one to five joules. But because the energy employed for cardioversion is some four to twenty times smaller than for defibrillation, the voltage in the former case is correspondingly smaller. Low voltages in the later portions of a pulse are known, however, to be ineffective in terminating tachycardia, and even induce fibrillation. It is worthwhile to provide some background for this observation:

Defibrillation, or causing the cessation of chaotic and uncoordinated contraction of the ventricular myocardium by application of an electrical direct current and voltage, in its most primitive form goes back to the last century. [J. L. Prevost and F. Batelli, "Sur Quelques Effets des Descharges Electriques sur le Couer des Mammifers," *Comptes Rendus Hebdomadaires des Seances de L'Acadmie des Sciences*, Vol. 129, p. 1267, 1899.] Because of the large currents required for defibrillation, large-area electrodes are employed. [A. C. Guyton and J. Satterfield, "Factors Concerned in Defibrillation of the Heart, Particularly through the Unopened Chest," *Am. J. of Physiology*, Vol 167, p. 81, 1951.]

For reasons of simplicity and compactness, capacitor-discharge systems are almost universally used in defibrillation. The discharge of a capacitor C through a resistance R results in a curve of voltage versus time (and hence, of current versus time as well) that is a declining exponential function (illustrated by the dotted curve in FIG. 1), with a characteristic time given by the product RC. But it has also been recognized for some time that the long-duration, low-amplitude "tail" of the capacitor-discharge pulse is detrimental. [J. C. Schuder, G. A. Rahmoeller, and H. Stoeckle, "Transthoracic Ventricular Defibrillation with Triangular and Trapezoidal Waveforms," *Circ. Res.*, Vol. 19, p. 689, October 1966; W. A. Tacker, et al., "Optimum Current Duration for Capacitor-discharge Defibrillation of Canine Ventricles," *J. Applied Physiology*, Vol 27, p. 480, October, 1969.] Although the exact reason for this detrimental effect is not known, plausible speculations exist, with one possibility being that field heterogeneities cause arthythmias in significantly large regions of the heart. [P S Chen, et al., "The Potential Gradient Field Created by Epicardial Defibrillation Electrodes in Dogs," *Circulation*, Vol. 74, p. 626, September 1986. ] A convenient way to eliminate the low-amplitude "tail" of a capacitor discharge is by switching, which is to say, simply opening the capacitor-load circuit after a predetermined time, or else when voltage has fallen to a particular value, as illustrated by the solid curve in FIG. 1. For this reason, the time-truncated capacitor discharge has been extensively used after its effectiveness was first demonstrated. [J. C. Schuder, et al., "Transthoracic Ventricular Defibrillation in the Dog with Truncated and Untruncated Exponential Stimuli," *IEEE Trans. Biom. Eng.*, Vol. BME-18, p. 410, November 1971.]

Two methods for specifying a time-truncated capacitor-discharge pulse in defibrillation systems have been extensively used. But neither method has involved systematic optimization of the pulse. Some manufacturers such as Medtronic (in their PCD product) simply specify pulse duration (as illustrated by d in FIG. 1), although the physician can choose and adjust the value. A typical value might be a programmable duration of 7 ms. Other manufacturers such as Cardiac Pacemakers (in their Ventak product) specify the relative amount of voltage decline at the time of truncation, with a typical value of the decline being 65% of the initial voltage, as illustrated in FIG. 2. It has become customary to use the term tilt to describe the relative amount of such voltage decline, expressed either as a decimal fraction or a percentage. In algebraic language, $$\text{tilt} = (V_{initial} - V_{final})/V_{initial}. \qquad \text{Eq. 1}$$

As a specific illustration of prior-art practice, one can cite a CPI system that uses a 140-microfarad capacitor for defibrillation. When used with largearea electrodes that typically yield a cardiac electrical resistance of 50 ohms, the system displays an RC time constant of 7 milliseconds. Using the specification of 65% tilt, one obtains a pulse duration of approximately 7 milliseconds, the RC time. But since they (arbitrarily) specify the same tilt specification for cardioversion, and since using the same RC system leads to the same pulse duration, it follows that the final voltage of the cardioversion pulse at the time of truncation can be as low as 40 to 50 volts, depending upon the cardioversion energy chosen. In particular, for a 1-joule pulse from the CPI system, the trailing voltage is 43 volts. Clinical experience with cardioversion pulses having durations in this vicinity shows an effectiveness of only 50 to 80 percent.

In addition to the hazard of supplying such a low voltage to the heart, this prior art constitutes a waste of energy. In tachycardia, heart cells that must be reset are in the state of diastole, a task requiring less energy than resetting cells that are in systole, as in the case of ventricular fibrillation. This fact is reflected in the lower energies typically chosen for cardioversion, but permits a further reduction of the pulse duration without sacrificing effectiveness, and while eliminating the dangerous low-voltage tail from the cardioversion pulse.

A characteristic time associated with far-field diastolic stimulation is in the neighborhood of 1 millisecond. Hence the prior-art cardioversion pulses are dramatically longer than the cardioversion pulses are dramatically longer than the optimum. (Far-field electrodes are relatively large-area electrodes, as distinguished from "point-source" electrodes such as those used in pacing.) The elucidation of this characteristic time employs the concept of chronaxie, that requires some background explanation:

The foundation for defining such a characteristic time is a family of mathematical neurophysiological models for tissue stimulation going back to the turn of the century, with the first important such model having been developed by Weiss. [G. Weiss, "Sur la Possibilite de Rendre Comparable entre Eux les Apparelis Suivant a l'Excitation Electrique," *Arch. Ital. de Biol.,* Vol. 35, p. 413, 1901.] He employed the ballistic-rheotome technique for pulse generation, wherein a rifle shot of known velocity is used to cut two wires in sequence, their spacing being set and measured. Cutting the first wire eliminated a short from a dc source, causing current to flow through the tissue under test, and cutting the second wire opened the circuit, terminating the pulse applied. Converting the electrical data into charge delivered by the pulse, Weiss found that the charge Q needed for stimulation was linearly dependent on pulse duration, d. Specifically, $$Q = k_1 + k_2 d.$$ Eq. 2.

Subsequently and similarly, the physiologist L. Lapicque collected substantial amounts of data on the amount of current required to for tissue stimulation, using constant-current pulses of various durations. [L Lapicque, "Definition Experimentelle de l'excitabilite," *Proc. Soc. de Biol,* Vol 77, p. 280, 1909.] Lapicque established an empirical relationship between the current I and the pulse duration d, having the form $$I = K_1 + (K_2/d).$$ Eq. 3.

(Note that multiplying this expression through by d yields an expression in charge rather than current, identically the equation given by Weiss. Thus $K_1 = k_1/d$ and $K_2 = k_2 d$.) Similar and confirming studies were carried out a few decades later. [H. Fredericq, "Chronaxie: Testing Excitability by means of a Time Factor," *Physiol Rev.,* Vol 8, p. 501, 1928.]

Equation 3 of Lapique shows that the necessary current and the pulse duration are related by a simple hyperbola, shifted away from the origin by the amount of the constant term $K_1$. Hence the stimulating current required in a pulse of infinite duration is $K_1$, a current value Lapicque termed the rheobase. Shortening the pulse required progressively more current, and the pulse duration that required a doubling of current for excitation, or $2K_1$, he termed the chronaxie, $d_c$. Substituting $2K_1$ and $d_c$ into Eq. 3 in place of I and d, respectively, yields $$d_c = K_2/K_1$$ Eq. 4

Lapicque's model described cell stimulation, rather than defibrillation, but Bourland demonstrated that defibrillation thresholds in dogs and ponies followed the Lapicque model, provided average current is used in the exercise. [J. D. Bourland, W. Tacker, and L. A. Geddes, "Strength-Duration Curves for Trapezoidal Waveforms of Various Tilts for Transchest Defibrillation in Animals," *Med. Instr.,* Vol 12, p. 38, 1978.] In a companion paper, the same workers showed that average current, $I_{ave}$, is a useful and consistent measure of defibrillation effectiveness for time-truncated pulses of a given duration through a substantial range of durations, from 2 to 20 milliseconds; in other words, so long as the exponential "tail" is eliminated, pulse effectiveness is not very dependant upon waveform details. [J. D. Bourland, W. Tacker, and L. A. Geddes, "Comparative Efficacy of Damped Sine Waves and Square Wave Current for Transchest Defibrillation in Animals," *Med Instr.,*Vol. 12, p. 42, 1978.] The defibrillation chronaxie for the heart is usually between 2 milliseconds and 4 milliseconds, as is borne out by a substantial fund of published data. [See co-pending application by Kroll and Smith, Optimal-Pulse Defibrillator.] For cardioversion the chronaxie is approximately 1 millisecond.

SUMMARY OF THE INVENTION

The general purpose of the present invention is a process for waveform optimization. It is based upon the models of Lapicque and Weiss, and the finding of Bourland. To do this, one first defines a "sufficiency ratio," the ratio of Bourland's ruling average current and the current needed for defibrillation according to the Lapicque model for a heart of a given $K_1$, rheobase current, and a given $K_2$, a charge. Algebraically, $$\text{Sufficiency ratio} = I_{ave}/(K_1 + K_2/d)$$ Eq. 5.

It is simply the ratio of Bourland's available therapeutic current (or the average current $I_{ave}$) to the current required according to the Lapicque formulation. Hence for a ratio of unity, the waveform of average current $I_{ave}$ and duration d will be able to defibrillate a heart characterized by $K_1$ and $K_2$. To review briefly, recall that the current $K_1$ and the charge $K_2$ characterize the sensitivity of particular tissue to electrical stimulation. The smaller these quantities are, the more sensitive is the tissue in question to electrical stimulation. The quotient of these two quantities yields a characteristic time, the chronaxie, which does not by itself indicate sensitivity or insensitivity.

Multiplying Eq. 5 through by the rheobase current $K_1$ yields an expression that of course has dimensions of amperes; noting from Eq. 4 that $K_1 d_c = K_2$, makes it possible to eliminate the heart-characterizing quantities $K_1$ and $K_2$ from this expression:

$$[I_{ave}/(1 + K_2/K_1 d)] = [I_{ave}/(1 + d_c/d)]$$ Eq. 6.

Thus, one has an expression in the two pulse-characterizing quantities $I_{ave}$ and d, and in one heart-characterizing quantity, $d_c$, the chronaxie time. Note that for an infinite pulse duration, this current simply equals the average current $I_{ave}$, but for a pulse of finite duration, it will be smaller than $I_{ave}$. This current, therefore, measures the effectiveness of a particular waveform in defibrillating a particular heart. For this reason the inventors have named it have named it the effective current or $I_e$, so that the defining equation is $$I_e I_{ave}/(1 + d_c/d)$$ Eq. 7

Note further that $I_e$ would be the same as $I_{ave}$ if one had a zero value of chronaxie time, $d_c$. In this sense, Eq. 7 constitutes a correction from actual average current necessitated by the chronaxie phenomenon. The effective current $I_e$ can be expressed in several ways:

$$I_e = [I_{ave}d/(d_c+d)] = [(delivered\ charge)/(d_c+d)] = CV_i(tilt)/(d_c+d) \qquad \text{Eq. 8.}$$

Applying this formulation to a prior-art system employing C=140 microfarad, tilt=0.65, $V_i$=125 volts, and an interelectrode resistance of R=50 ohms (for a pulse duration of about 7 milliseconds) yields an effective current of $$I_e = [(140\ F)(125\ V)(0.065)/(1\ ms + 7\ ms)] = 1.42\ A \qquad \text{Eq. 9.}$$

It is convenient to illustrate the kind of information obtainable from this analysis by using the hypothetical (and easy to calculate) case of a rectangular current pulse employed for cardioversion. With a current I delivered to the (cardiac) load resistance R, we can write the energy E of the pulse as $$E = I R d, \qquad \text{Eq. 10}$$

so that $$I = \sqrt{(E/Rd)} = I_{ave}. \qquad \text{Eq. 11}$$

The object, now, is to maximize the effective current $I_e$, which is given by $$I_e = [I_{ave}/(1 + d_c/d)] = \sqrt{(E/Rd)}\ /(1 + d_c/d) \qquad \text{Eq. 12}$$

or, $$I_e = \sqrt{(Ed/R)}\ /(d_c + d). \qquad \text{Eq. 13}$$

Differentiating this expression with respect to d and equating the result to zero yields $$d = d_c. \qquad \text{Eq. 14.}$$

Thus, for a truly rectangular pulse, the optimal duration is simply the chronaxie time. This result has intuitive appeal, because one is matching the pulse duration to the natural time constant of the cardiac system. This result is known in pacing [J. A. Pearce, et al., "Myocardial Stimulation with Ultrashort Duration Pulses," PACE Vol 5, p 52;, Jan.-Feb. 1982], and has been derived for defibrillation as well. It was, in fact, noted by Lapique. Hence our result using the concept of effective current is consistent with prior knowledge.

It is further instructive to calculate the current in the hypothetical 1-joule rectangular pulse having a duration of 1 millisecond for comparison with the effective current obtained above for the prior-art truncated capacitor-discharge pulse having a duration of 7 milliseconds. From Eq. 10, $$I = [(1\ J)/(50\ ohm)(1\ ms)] = 4.47\ A. \qquad \text{Eq. 15.}$$

Thus the 1-joule in this example yields an effective current over three times greater than that of a 1-joule pulse of the prior art, illustrating the virtue of a short pulse in spite of the hypothetical nature of the waveform in the present example.

Given that a truncated capacitor-discharge pulse is used in real life, the next task is to optimize such a pulse for cardioversion. A capacitor C will be charged to a voltage $V_i$ and discharged into a cardiac load resistance R, with time truncation to yield a pulse duration d. This fixed capacitor will be charged to a fixed voltage, resulting in the storage of a fixed energy in the capacitor. Neglecting converter losses, this energy will equal the energy drawn from the battery. The amount of energy taken from the battery for a given shock is limited, because we want to be able to provide several cardioversion shocks. The challenge is to maximize the effective current $I_e$ for a given energy stored in the capacitor.

Because the waveform is a declining exponential function, and given that RC=t, the system time constant, tilt as a decimal fraction can be written as follows:

$$tilt = 1 - \exp(-d/t) \qquad \text{Eq. 16.}$$

Combining this expression and Eq. 8 yields $$I_3 = CV_i[1 - \exp(-d/t)]/(d_c + d) \qquad \text{Eq. 17.}$$

It is clear the $I_e$ vanishes at both extremes of d, so the intermediate extremum must be a maximum, defining explicitly the optimum waveform that can be achieved by varying pulse duration with a particular average current. To determine this optimum pulse duration, set.

$$(dI_e/dd) = 0 = \{CV_i(d_c+d)[1/t\exp(-d/t)] - [1 - \exp(-d/t)]\}/(d_c+d)^2 \qquad \text{Eq. 18.}$$

Hence, $$0 = \exp(-d/t)[(d_c+d)/t] - 1 + \exp(-d/t)$$
$$= -1 + \{[(d_c+d)/t] + 1\}\exp(-d/t) \qquad \text{Eq. 19.}$$

Using the system time constant t=RC for normalization yields $$z = d/t, \qquad \text{Eq. 20}$$

and $$= d/t. \qquad \text{Eq. 21.}$$

Using these definitions, $$(z + a + 1)[\exp(-z)] - 1 = 0 \qquad \text{Eq. 22.}$$

Next multiply through by $-e^{-z}$ to obtain the simplified equation whose root is sought:

$$[\exp(-z)] - z - a - 1 = 0 \qquad \text{Eq. 23.}$$

Because the equation is transcendental, it cannot be solved in closed form, so define the function on the left-hand side as f(z) and the first approximation for its root as $z_0$. The Newton-Raphson method gives an approximate value for the root as $$z' = z_0 - f(z_0)/f'(z_0) \qquad \text{Eq. 24.}$$

Experience shows that waveforms with a tilt of about 65% are effective, and this corresponds to d=t, or $z_0$=1. Hence and appropriate approximate root is $$z' = [z_0 - f(z_0)/f'(z_0)] = 1 - (e - 1 - 1 -)/(e = 1) \qquad \text{Eq. 25.}$$

Denormalization yields $$d = (t + d_c)/(e - 1). \quad \text{Eq. 26}$$

for the approximate optimum value of pulse duration d as a function of chronaxie $d_c$ and system time constant t. Carrying through the optimization numerically shows that this estimate is valid within 0.2% for typical values of R, C, and $d_c$. Even for extreme values of these system and heart parameters, the approximate value of optimum duration produces a value for the current $I_e$ that is within 2% of the optimum. Since $(e-1)=1.72$, the optimum pulse duration is approximately (and somewhat larger than) the average of the system's time constant t and the heart's characteristic time $d_c$. In other words, the optimum pulse duration is a compromise between the two characteristic times involved.

Equation 26 gives the optimal value of pulse duration d, which is to say, it gives the value of d that maximizes effective current $I_e$. Placing that value of d in the expression for $I_e$, Eq. 17, and noting that $RC = t$, yields $$I_e = CV_i \frac{\{1 - \exp[(1 + d_c/RC)/(1 - e)]\}}{[(RC + d_c)/(e - 1)] + d_c}. \quad \text{Eq. 27}$$

Since the energy E initially stored in the capacitor is given by $$E = (\tfrac{1}{2})CV_i, \quad \text{Eq. 28}$$

it follows that the coefficient of Eq. 27 can be written as $$CV_i = \sqrt{(2EC)}. \quad \text{Eq. 29}$$

Thus the expression for effective current, Eq. 27, can be written as the product of two functions. One is simply $\sqrt{E}$, and the other is a function of system variables including C, but excluding E. In other words, there exists an optimal capacitance for maximizing effective current that is independent of the energy to be stored in it; one should use that capacitance value and then set the desired energy by adjusting the initial voltage $V_i$.

The problem thus reduces to finding the maximum value of the transcendental fraction in Eq. 27 as a function of C. Differentiating it with respect to C, setting the result equal to zero, and solving the equation thus obtained numerically for C yields $$C = (0.8)d_c/R, \quad \text{Eq. 30}$$

an expression that is accurate to 1% over a broad range of the exogenous variables R and $d_c$. This is an eminently reasonable result because it indicates that for best performance, the RC product should be close to the innate time constant (chronaxie) of the myocardial cells. This is the reason that the initially stored energy and the optimum capacitance are independent of one another rather than being coupled. Assuming $d_c = 1.0$ millisecond, the chronaxie value, and an interelectrode resistance of $R = 50$ ohms yields an optimal capacitance of $C = 16$ microfarads. The associated optimal pulse duration is $d = 1.38$ millisecond, leading to tilt = 82%.

To assess the cardioversion efficacy of a pulse thus derived from a smaller-than-standard capacitor, one can calculate the effective current $I_e$ from a 1-joule pulse so derived for comparison with that of the 1-joule pulse of the prior art calculated in Eq. 9. From Eq. 8, in the present case, with $= 353.6$ volts, $$I_e = (16\ \text{microfarad})(353.6\ V)(0.82)/(1+1.38)ms = 1.95\ A \quad \text{Eq. 31.}$$

This is a significant improvement over the prior-art value of 1.42 amperes for effective current from a 1-joule pulse. To emphasize this improvement further, let us calculate the stored energy E that would be needed in the prior-art with its 140-microfarad capacitor and 65% tilt to match the effective-current result in Eq. 31. An initial voltage of $V_i = 171.4$ V would be necessary, and that leads to an initial stored energy of $E = 2.06$ joule. Thus, more than twice the stored energy would be necessary!

All of the discussion and calculations above have concerned cardioversion using a monophasic pulse, like that illustrated by the solid line in either FIG. 1 or FIG. 2. Furthermore, one can focus on the central element in the present invention, which is to provide a capacitor that is smaller, and hence more effective for cardioversion, than the defibrillation capacitor. The circuitry needed for handling the two capacitors is depicted schematically in FIG. 3. Closing and then opening the switch S1 will first charge and then isolate the defibrillation capacitor C1. Closing and then opening the switch S2 will initiate and then truncate the monophasic defibrillation pulse. In a similar way, the switch S3 charges and isolates the cardioversion capacitor C2, and switch S4 initiates and truncates the monophasic cardioversion pulse.

Cardioversion, however, like defibrillation, can be accomplished with "multiphasic" pulses. An important example of such a case is the biphasic waveform, illustrated in FIG. 4. In such a waveform, the optimal properties calculated above for a monophasic pulse are designed into the initial phase. A standard way of generating the biphasic waveform is illustrated schematically in FIG. 5. The capacitor C, previously charged by methods like those illustrated in FIG. 3, but omitted from FIG. 5, is discharged into the heart by closing switches S1 and S4. Then these two switches are opened to terminate the first "phase" or positive pulse in FIG. 4, and simultaneously, the switches S2 and S3 are closed to continue the discharging of the capacitor C, but delivering voltage and current of the opposite polarity to the heart. Opening the last named switches terminates the second or negative phase of the biphasic waveform.

In a further embodiment of the present invention, the smaller capacitor can be used to assist the larger capacitor in its defibrillation task. Charge delivery from the smaller capacitor will take place after voltage on the larger had dropped sufficiently. In the case of biphasic defibrillation, this will usually occur during the second phase.

It must be stressed that the identification of optimally effective properties in a cardioversion waveform and the system for generating the waveform has at least two very welcome effects. First, it benefits the patient by providing more efficacious therapy, and second, it conserves battery energy. Thus reducing the demand on the battery permits a reduction of its size, which is a welcome occurrence in the process of designing an implantable cardioverter-defibrillator. While it is true that an extra capacitor and additional circuitry are needed to implement the present invention, it is also true that circuitry traditionally requires little physical volume. And it is further true that the added capacitor, which typically will be an order of magnitude smaller than the defibrillation capacitor, and also will carry an appreciably relaxed voltage specification, will require only modest space.

One significant aspect and feature of the present invention is a cardioversion waveform delivered from a capacitor significantly smaller than a typical defibrillation capacitor.

Another significant aspect and feature of the present invention is a cardioversion waveform of optimum effective current as well as optimum duration.

Still another significant aspect and feature of the present invention is the use of charge in the relatively small cardioversion capacitor to add to that delivered from the defibrillation capacitor in the latter portions of a defibrillation waveform, whether monophasic or biphasic.

Yet another significant aspect and feature of the present invention is to avoid low-voltage and hence hazardous trailing portions in both monophasic and multiphasic waveforms.

Still another significant aspect and feature of the present invention is the extension of battery life by using its energy more efficiently.

A still further significant aspect and feature of the present invention is a potential reduction in ICD size and weight by reducing the demand for battery energy.

Having thus described embodiments and features of the present invention, we note that it is a principal object of the invention to achieve a cardioversion waveform that is more effective than one that a defibrillation capacitor is able to deliver.

One object of the invention is delivery of a cardioversion pulse of improved effectiveness.

A further object of the invention is to employ a cardioversion pulse of optimal duration and effective current.

A still further object of the invention is to provide sufficiently versatile circuit to permit the cardioversion capacitor to assist the defibrillation capacitor when such help is needed.

Yet a further object of the invention is to avoid low-voltage and hence hazardous trailing portions in both monophasic and multiphasic waveforms.

An additional object of the invention is to diminish the demands on an ICD battery.

BRIEF DESCRIPTION OF THE DRAWINGS

Other objects of the present invention and many of its attendant advantages will be readily appreciated as the invention becomes better understood by reference to the following descriptions, when considered in connection with the accompanying drawings in which like reference numerals designate like parts throughout the figures thereof, and wherein.

DETAILED DESCRIPTION OF THE PREFERRED EMBODIMENTS

FIG. I illustrates a monophasic waveform 10 of a preferred-embodiment monophasic pulse for cardioversion of the present invention, specified by an initial voltage 12 and a duration 14, and also illustrates the monophasic pulse in relation to a corresponding untruncated capacitor-discharge waveform 16.

Figure 2:
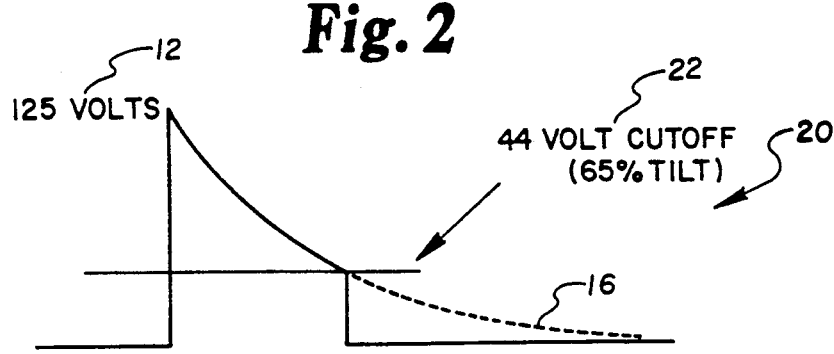
FIG. 2 illustrates the same monophasic pulse for cardioversion in relation to an untruncated capacitor-discharge waveform, and a second method for specifying truncation.

FIG. 2 illustrates the waveform 20 of a preferred embodiment monophasic pulse for cardioversion of the present invention, specified by means of an initial voltage 12 and a tilt 22, and also illustrates the monophasic pulse in relation to a corresponding untruncated capacitor-discharge waveform 16.

Figure 1:
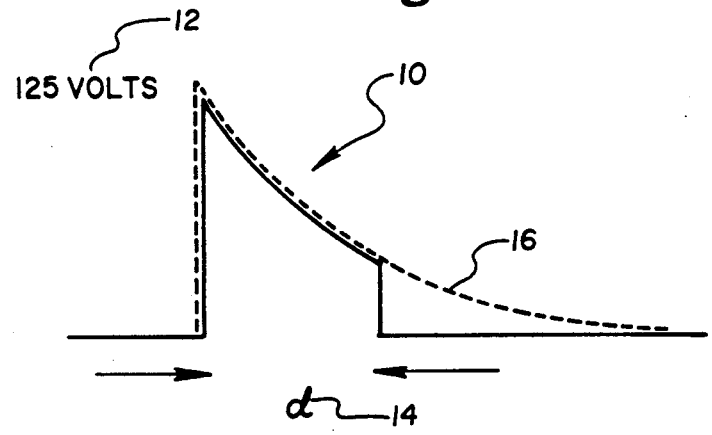
FIG. 1 illustrates a monophasic pulse for cardioversion in relation to an untruncated capacitor-discharge waveform, and one method for specifying truncation.
Figure 3:
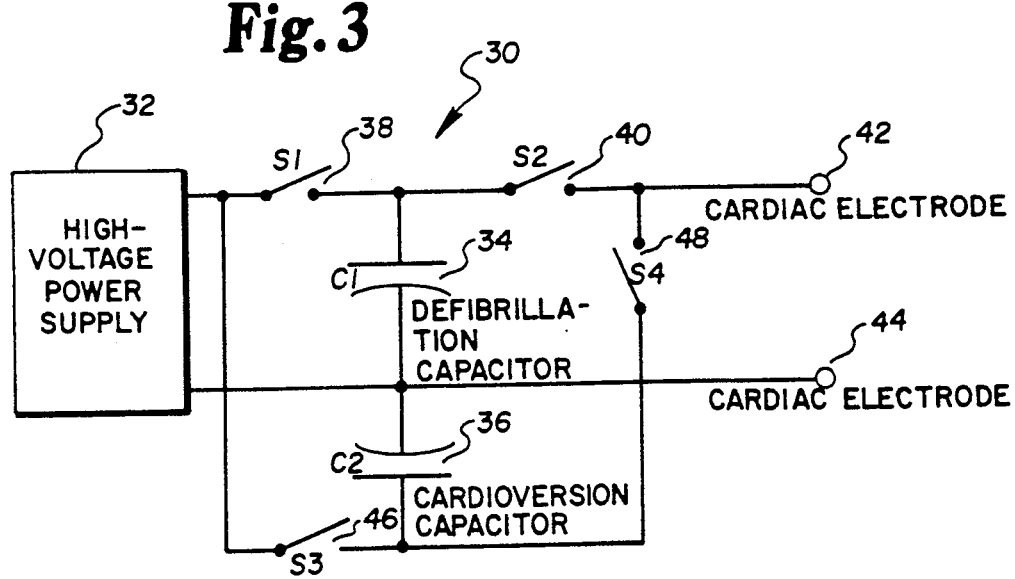
FIG. 3 illustrates a representation of a circuit for generating the monophasic cardioversion pulse of FIGS. 1 and 2 as well as a higher-energy defibrillation pulse.

FIG. 3 illustrates a simplified representation 30 of a circuit for generating the monophasic cardioversion pulses 10 and 20 of FIGS. 1 and 2, respectively, as well as generating a higher-energy monophasic defibrillation pulse. The circuit comprises high-voltage charging circuitry 32 for the capacitors 34 and 36. The switch 38 is closed to charge the defibrillation capacitor 34, and opened to isolate it. The switch 40 is closed to deliver the defibrillation pulse to the cardiac electrodes 42 and 44 and is opened to truncate the monophasic pulse. In a similar way, the switch 46 is closed to charge the cardioversion capacitor 36, and opened to isolate it. The switch 48 is closed to deliver the cardioversion pulse to the cardiac electrodes 42 and 44, and is opened to truncate the monophasic pulse.

Figure 4:
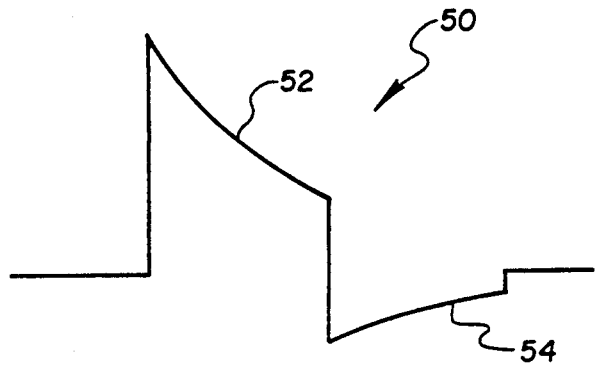
FIG. 4 illustrates an example of a biphasic pulse for cardioversion.

FIG. 4 illustrates the waveform 50 of an example of a biphasic pulse for cardioversion of the present invention, comprising a first phase 52 and a contiguous second phase 54.

Figure 5:
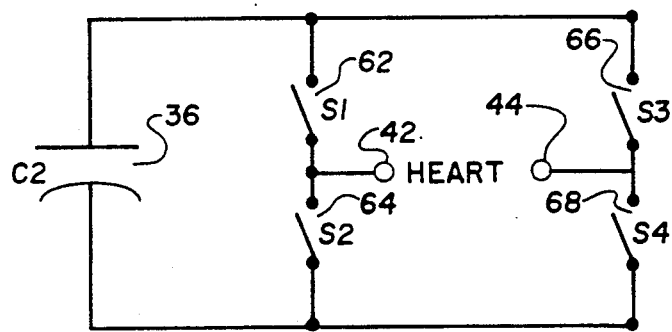
FIG. 5 illustrates a representation of a circuit for generating the biphasic cardioversion pulse of FIG. 4.

FIG. 5 illustrates representation 60 of a circuit for generating the biphasic cardioversion waveform 50 of FIG. 4, comprising a capacitor 36, the four switches 62, 64, 66, and 68 that are able to reverse polarity in going from the first phase 52 of FIG. 4 to the second phase 54 of FIG. 4 for purposes of delivering the biphasic waveform 50 of FIG. 4 to the cardiac electrodes 42 and 44. In operation, the switches 62 and 68 close to initiate the first phase 52 of the biphasic waveform 60 and open to terminate the first phase 52, whereupon the switches 64 and 66 close at the same instant that the switches 62 and 68 open, thus initiating the second phase 54 of the biphasic waveform 60 and open to terminate the second phase 54.

MODE OF OPERATION

The process is based upon the pioneering neurophysiological models of Lapicque and Weiss. This model is further able to determine mathematically the optimum pulse duration, d, for a truncated capacitor-discharge waveform employed for cardioversion. It comprehends the system time constant, RC, where R is tissue resistance and C is the value of the capacitor being discharged, and also the heart's cardioversion chronaxie, $d_c$, defined by Lapicque, which is a characteristic time associated with the stimulation of myocardial tissue. The model and analysis find the optimum pulse duration to be roughly one millisecond. The concept of effective current that is another feature of the model used here further permits in the present invention a determination of optimal capacitance for cardioversion, which turns out to be independent (through wide ranges) of the energy that is to be employed. This finding reveals that the optimal capacitance is, for the examples in the present invention, some nine times smaller than a typical defibrillation capacitor. Thus, the provision of an additional small capacitor for cardioversion helps to conserve battery energy in an ICD (where conservation is especially important) by delivering cardioversion pulses of optimal effectiveness. An additional feature of the present invention is use of the added small capacitor as a booster in defibrillation procedures.

Various modifications can be made to the present invention without departing from the apparent scope hereof.

I claim:

1. An improved apparatus for producing cardioversion defibrillation waveforms to be delivered to at least two implantable electrodes in a human patient in response to a sensing of a cardiac dysrhythmia in the patient the apparatus including a first capacitor means having a first capacitance value for storing a first amount of electrical energy, means for charging the first capacitor means to the first amount of electrical energy, and switch means for selectively controlling a discharge of the first capacitor means through the at least two electrodes to produce a defibrillation waveform, the improvement comprising:

a second capacitor means separate from the first capacitor means and having a second capacitance value for storing a second amount of electrical energy, the second capacitance value and the second amount being of smaller values than the first capacitance value and the first amount of electrical energy;

means for charging the second capacitor means to the second amount of electrical energy; and switch means for selectively controlling a discharge of the second capacitor means through the at least two electrodes to produce a cardioversion waveform having at least one pulse having a pulse duration.

2. The apparatus of claim 1 wherein the pulse duration is a value derived from a predetermined total decay percentage of the first or second amount of electrical energy.

3. The apparatus of claim 2 wherein the predetermined total decay percentage of the preselected amount of electrical energy stored in the second capacitor is a value between 60% and 90%.

4. The apparatus of claim 3 wherein the predetermined total decay percentage of the preselected amount of electrical energy stored in the second capacitor is a value between 80% and 84%.

5. The apparatus of claim 1 wherein the pulse duration is a predefined time period.

6. The apparatus of claim 5 wherein the pulse duration is a value between 0.5 millisecond and 3 milliseconds.

7. The apparatus of claim 6 wherein the pulse duration is a value between 1.1 millisecond and 1.6 milliseconds.

8. The apparatus of claim 7 wherein the pulse duration is a value between 1.3 millisecond and 1.5 milliseconds.

9. The apparatus of claim 1 wherein the pulse duration is approximately the average of:

a first time constant that is a system time constant, RC, of the apparatus, where R is an inter-electrode resistance value and C is the first or second capacitance value of the first or second capacitor means, and a second time constant that is an average cardioversion chronaxie characteristic time, $d_c$ of the heart of the human patient.

10. The apparatus of claim 1 wherein the optimal pulse duration is determined by the switch means for a first phase of a multiple phase pulse, said first phase of a consistent polarity.

11. The apparatus of claim 10 wherein the optimal pulse duration for the first phase is automatically set by the apparatus to be approximately the average of:

a first time constant that is a system time constant, RC, of the apparatus where R is an inter-electrode resistance value and C is the first or second capacitance value of the first or second capacitor means, and a second time constant is an average cardioversion chronaxie, $d_c$ of the heart of the human patient.

12. The apparatus of claim 10 wherein the optimal pulse duration for the first phase is a value between 0.5 millisecond and 3 milliseconds.

13. The apparatus of claim 12 wherein the optimal pulse duration for the first phase is a value between 1.1 millisecond and 1.6 milliseconds.

14. The apparatus of claim 13 wherein the optimal pulse duration for the first phase is a value between 1.3 millisecond and 1.5 milliseconds.

15. The apparatus of claim 10 wherein the optimal pulse duration is automatically set by the apparatus to be a value derived from a predetermined total decay percentage of the first or second amount of electrical energy of the first phase of the multiple phase pulse that is a value between 60% and 90%.

16. The apparatus of claim 15 wherein the total decay percentage of the first phase of the multiple phase pulse is a value between 80% and 84%.

17. The apparatus of claim 10 wherein the cardioversion defibrillation waveform comprising two pulses, at least one of which is biphasic, where a first pulse has the optimal pulse duration and is delivered from the second capacitor means.

18. The apparatus of claim 1 wherein cardioversion waveforms are derived from the second capacitor means and defibrillation waveforms are delivered from the first capacitor means.

19. The apparatus of claim 1 wherein the defibrillation waveform is comprised of the first amount of electrical energy delivered from the first capacitor means and the second amount of electrical energy delivered from the second capacitor means at a preselected time after the delivery of the first amount of electrical energy is begun.

20. An improved method for operating a cardioverter defibrillator system connected to at least two implanted electrodes located in a human patient to treat a cardiac dysrhythmia, the method including the steps of sensing a cardiac dysrhythmia and in response delivering an electrical waveform to the at least two implanted electrodes to treat the cardiac dysrhythmia, the improvement comprising the system-implemented steps of:

(a) in response to the sensing of a fibrillation dysrhythmia, selectively charging and discharging a first capacitor to produce a defibrillation waveform that is time-truncated at a particular duration for defibrillation, and;

(b) in response to the sensing of a tachycardia dysrhythmia, selectively charging and discharging a second capacitor separate from the first capacitor to produce a cardioversion waveform that is time-truncated at a lesser duration than the duration of the defibrillation waveform.

21. The method of claim 20 wherein the duration of the defibrillation and cardioversion waveforms is determined by a percentage decay of an electrical charge stored in the first and second capacitors, respectively.

22. The method of claim 21 wherein the percentage decay is a value between 60% and 90%.

23. The method of claim 21 wherein the percentage decay is a value between 80% and 84%.

24. The method of claim 20 wherein the duration of the defibrillation and cardioversion waveforms is measured by a first phase of a biphasic pulse for defibrillation waveforms, and by a first phase of a biphasic pulse for cardioversion waveforms, respectively.

25. The method of claim 20 wherein the duration of the defibrillation and cardioversion waveforms is measured by a first phase of a multiphasic pulse for defibrillation waveforms, and by a first phase of a multiphasic pulse for cardioversion waveforms, respectively.

26. The method of claim 20 wherein the duration of the defibrillation and cardioversion waveforms is a predefined time period.

27. The method of claim 20 wherein the duration defibrillation and cardioversion waveforms is automatically set by the system to be approximately the average of:

a first time constant that is a system time constant, RC, of the apparatus, where R is an interelectrode resistance value and C is a capacitance value of the first or second capacitors, and a second time constant that is an average cardioversion chronaxie characteristic time, $d_c$ of the heart of the human patient.

28. The method of claim 20 wherein the duration of the cardioversion waveforms is a value between 0.5 millisecond and 3 milliseconds.

29. The method of claim 28 wherein the duration of the cardioversion waveforms is a value between 1.1 millisecond and 1.6 milliseconds.

30. The method of claim 29 wherein the duration of the cardioversion waveforms is a value between 1.3 millisecond and 1.5 milliseconds.

* * * * *